United States Patent [19]

Chahal

[11] Patent Number: 5,047,332
[45] Date of Patent: Sep. 10, 1991

[54] INTEGRATED PROCESS FOR THE PRODUCTION OF FOOD, FEED AND FUEL FROM BIOMASS

[75] Inventor: Devinder S. Chahal, Laval, Canada

[73] Assignee: Institut Armand-Frappier-Univ. of Quebec, Laval, Canada

[21] Appl. No.: 903,467

[22] Filed: Sep. 3, 1986

[51] Int. Cl.$^5$ .................. A23K 1/00; C12P 39/00; C12P 19/02; C12P 21/00
[52] U.S. Cl. .................. 435/42; 426/53; 426/54; 435/105; 435/165; 435/170; 435/171; 435/172.1; 435/251; 435/252; 435/252.1; 435/254; 435/262; 435/272; 435/274; 435/911; 435/913; 435/933; 435/945
[58] Field of Search .......... 435/42, 105, 165, 170, 435/251, 68, 171, 252, 172.1, 267, 911, 252.1, 913, 804, 272, 254, 274, 933, 945; 426/53, 55, 56, 60

[56] References Cited

U.S. PATENT DOCUMENTS

| | | | |
|---|---|---|---|
| 4,281,063 | 7/1981 | Tsao et al. | 435/99 |
| 4,294,929 | 10/1981 | Solomons | 435/254 |
| 4,370,351 | 1/1983 | Harper | 426/7 |
| 4,472,504 | 9/1984 | Gallo | 435/209 |
| 4,642,287 | 2/1987 | Inoi et al. | 435/99 |

FOREIGN PATENT DOCUMENTS 1124131  5/1982  Canada ...................... 99/27

OTHER PUBLICATIONS

Chahal, D. S., Biotechnol. Bioeng. Symp., 1984 (14), pp. 425–433.

*Primary Examiner*—Richard A. Schwartz
*Assistant Examiner*—Richard C. Peet
*Attorney, Agent, or Firm*—Fred A. Keire

[57] ABSTRACT

A feedstock containing a biomass such as lignocellulosic materials, e.g. forest biomass; agricultural residues; or manures, is pretreated and thereafter is fractionated into cellulose, lignin and hemicelluloses. New mutants are disclosed which include *Chaetomium cellulolyticum* IAF-101 (NRRL 18756), *Aspergillus* sp. IAF-201 (NRRL 18758), *Penicillum* sp. IAF-603 (NRRL 18759), and *Trichoderma reesei* QMY-1. With these new mutants and also known fungi including *Pleurotus sajor-caju* and other *Pleurotus* spp. unfractionated predetermined biomass is converted into feed. The same treatment can also be applied to hemicelluloses, and cellullose. Cellulose can also be hydrolyzed by means of a cellulase-system prepared from cellulose and *Tricoderma reesei* to prepare glucose which can be converted to alcohol with *Saccharomyces cerevisiae*, *Kluyveromyces* spp. and *Zymomonas mobilis*. The residual microbial biomass of these microorganisms from alcohol fermentation broth is also used as feed. The process is economical and non polluting.

14 Claims, 1 Drawing Sheet

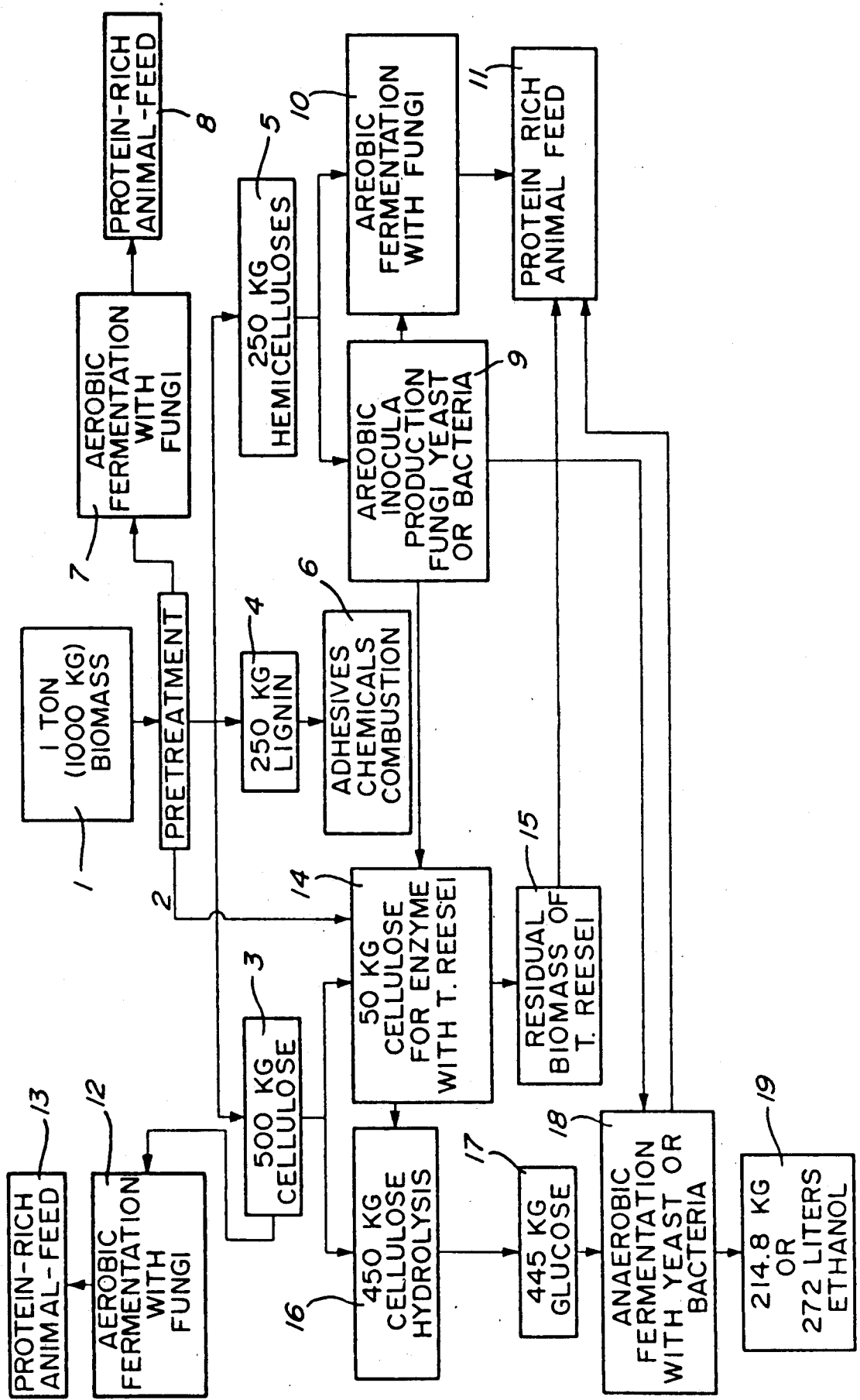

INTEGRATED PROCESS FOR THE PRODUCTION OF FOOD, FEED AND FUEL FROM BIOMASS

BACKGROUND OF INVENTION

1. Field of the Invention

This invention relates to an integrated process for the production of food, feed and fuel from biomass. More particularly, the present invention is directed to an improved process wherein the carbohydrate fractions of biomass are converted into protein-rich food for humans, protein-rich feed for animals and liquid fuel such as ethanol. On the other hand, the lignin fraction can be converted into adhesives, various chemicals or can be used as a burning fuel.

In the following description, concentrations of substances are expressed as wt/vol (weight per unit volume of total mixture), as vol/vol (volume per unit volume of total mixture), as wt/wt (weight per unit weight of total mixture on a dry basis).

The term biomass used herein includes lignocelluloses, which are mostly derived from crop residues, wood and wood residues. Generally speaking, biomass can be fractionated into cellulose, hemicelluloses and lignin. It is the most important source of organic carbon that can be used for bioconversion into food, feed and fuel. The term biomass also includes solid and liquid manures.

2. Description of Prior Art

In view of the world supply and demand of calories and proteins, the development of unconventional sources of food and feed is considered to be most important for mankind. Heavy demands of grain for the production of ethanol fuel would further aggravate present shortages. Moreover, escalating food/feed prices throughout the world have established the need for a high energy feed (70-75% digestability). It has already been proposed to produce high energy feed from poplar, and recently renewable biomass (especially forest biomass) has been found to be very attractive feedstock for the production of food, feed and also ethanol fuel.

The forest is a very important renewable wealth and forest biomass is produced in large quantities every year throughout the world. Similarly, large quantities of mill and logging residues are also available.

The biomass of plant origin, generally called lignocelluloses, contains 45-56% cellulose, 10-29% hemicelluloses, and 14-30% lignin. It would, therefore, appear that bioconversion of carbohydrates (75-50%) into animal feed rich in protein (40-47%) would save millions of dollars which are presently spent to import soybean as a source of protein to supplement animal feed. On the other hand, the composition of biomass of manures of animal origin varies considerably depending on the feed given to the animal. Usually, this source is rich in starch lipids, protein and microbial biomass, and also contains little cellulose, hemicelluloses and lignin. Similarly, the affluents from food factories are rich in starch, protein and minerals but contain very little cellulose, hemicelluloses and lignin.

In an article entitled "In Search of Microbial Food and Feed: *Chaetomium cellulolyticum*—the Obvious Answer", which I presented at the Symposium "New Sources of Food" of the National Meeting of AICHE at Denver, Col., Aug. 28-31, 1983, I indicated that the production of single cell protein SCP from biomass with *Chaetomium cellulolyticum* seems to be more promising than all the other microorganisms being tried in the world. *C. cellulolyticum* is a new fungus which I discovered in 1972 and is deposited at the ATCC under accession number of 32319. The taxonomy, morphology and physiology of this new fungus were reported in *Mycologia*, 68:600-610, 1976.

A few processes have been proposed or used to convert "lignocellulosic biomass" into protein-rich feed for humans and animals. However, they suffer with one or more of the following drawbacks.

1. In most cases the "lignocellulosic biomass" is pretreated with various processes to make it suitable for bioconversion into protein-rich feed by fermenting with various microorganisms. During these pretreatments lignin is to be removed; however, by doing so, almost all the hemicelluloses, which are a potential source of carbohydrates, are also removed. These hemicelluloses end up in a waste stream which creates pollution problems because of its very high Biological Oxygen Demand (BOD).

2. Most of the microorganisms used in such processes have poor conversion efficiency and a considerable amount of lignocelluloses are left utilized which cannot be separated from the final product thus lowering its value as protein supplement because of low protein content of the final product.

3. Some of the organims such as *Chaetomium cellulolyticum* ATCC 32319, being used in some processes for production of protein-rich feed for animals, has recently been found to produce toxic compounds.

The following Patents deal with a simple treatment of biomass with the known microorganism, *Chaetomium cellulolyticum* ATCC 32319.

U.S. Pat. No. 4,379,544
U.S. Pat. No. 4,401,060
U.S. Pat. No. 4,447,530
U.S. Pat. No. 4,526,791
Canadian Patent No. 1,124,131
Canadian Patent No. 1,129,709

The disadvantages associated with fuel ethanol production from "lignocellulosic biomass⇌ through enzymatic hydrolysis are the following:

1. Cost of enzyme production is very high.
2. Substrate conversion into sugars is low (about 50%).
3. Final concentration of sugars in the hydrolysate is 3-5% which may give 1.5-2.5% ethanol in the fermentation broth. This small quantity of ethanol in the broth is not economical for distillation into 95% ethanol.
4. Hemicelluloses are not properly utilized which end up in pollution stream. Although there are many methods to convert pure xylose (a major component of hemicelluloses into ethanol, none is capable to give more than 40% of theoretical yield from hemicelluloses.

SUMMARY OF INVENTION

It is an object of the present invention to provide new mutants which enable to obviate the problems associated with the prior art. The new mutants are the following:

*Chaetomium cellulolyticum* IAF-101 (NRRL 18756)
*Aspergillus* sp. IAF-201 (NRRL 18758)
*Penicillum* sp. IAF-603 (NRRL 18759)
*Trichoderma reesei* QMY-1 (NRRL 18760)

It is another object of the present invention to provide an integrated process for the production of food, feed and fuel from biomass involving the use of the above microorganisms and also *Pleurotus sajor-caju* and other Pleurotus spp., as well as other micro-organisms such as *Saccaromyces cerevisiae, Kluyveromyces* sp. and *Zymomonas mobilis* and the like.

It is another object of the present invention to provide a cellulase-system with high cellulase per unit volume, to give glucose and optionally ethanol.

It is another object of the present invention to utilize native cellulose derived from wood and/or crop residues as such or pretreated by physicochemical methods, such as with alkali, acid, steam at 100° C. or higher, and/or high pressure.

It is another object of the present invention to provide a hydrolysis of high concentrations of cellulose with the cellulase-system according to the invention, thereby enabling to obtain high concentrations of sugars for the economical fermentation and distillation of ethanol.

It is another object of the present invention to provide an integral process to produce inocula of the above microorganisms on hemicelluloses for food and feed production.

It is another object of the present invention to provide an inoculum of *Trichoderma reesei* on hemicelluloses for the production of an enzyme comprising a cellulase-system.

It is another object of the present invention to provide a process for treating biomass which comprises any suitable combination of the following steps:

a) pretreating said biomass to enable it to be fractionated into cellulose, lignin and hemicelluloses;

b) separating pretreated biomass into said cellulose, lignin and hemicelluloses.

c) providing inocula of *Chaetomium cellulolyticum* IAF-101 (NRRL) 18756), species of Pleurotus including *Pleurotus sajor-caju,* Aspergillus sp. IAF-201, (NRRL 18758 ) Penecillum sp. IAF-603 (NRRL 18759) *Trichoderma reesei* QMY-1, (NRRL 18760) yeast and bacteria by growing same on hemicellulose fraction obtained by separation from pretreated biomass;

d) innoculating another hemicellulose fraction obtained by separation from pretreated biomass with an inoculum selected from the group consisting of inocula of Chaetomium cellulolytium IAF-101, (NRRL 18756), Pleurotus, Aspergillus sp. IAF-201 (NRRL 18758) and Penicillum sp. IAF-603 (NRRL 18759) under aerobic fermentation conditions effective to produce protein-rich animal feed;

e) providing a fraction of pretreated biomass not subjected to separating step (b) and inoculating same th an inoculum of *Chaetomium cellulolyticum* IAF-101 (NRRL 18756), species of Pleurotus, Aspergillus sp. IAF-201 (NRRL 18758) and Penicillum sp. IAF-603 (NRRL 18759) under aerobic fermentation conditions effective to produce protein-rich animal feed;

f) treating a lignin fraction obtained in step (b) to produce adhesives and chemical products or burning same to produce heat or energy;

g) inoculating a cellulose fraction obtained by separation from pretreated biomass with an inoculum selected from the group consisting of inocula of *Chaetomium cellulolyticum* IAF-101 (NRRL 18756), species of Pleurotus, Aspergillus sp. IAF-201 (NRRL 18758) and Penicillum sp. IAF-603 (NRRL 18759) under aerobic fermentation conditions effective to produce protein-rich animal feed;

h) fermenting a fraction of pretreated biomass not subjected to separating step (b) or fractionated cellulose under aerobic conditions with *Trichoderma reesei* QMY-1 (NRRL 18760) to give a cellulase-system, hydrolyzing a cellulose fraction obtained in step (b) with said cellulase-system to give glucose, and fermenting said glucose with an inoculum selected from said inocula of yeasts and bacteria to give ethanol.

The glucose obtained could be used for the production of pharmaceuticals or any other fermentation products.

BRIEF DESCRIPTION OF DRAWINGS

The invention will now be described with reference to the annexed drawings in which:

FIG. 1 is a flowsheet illustrating the integrated process according to the invention.

MICROORGANISMS USED IN INTEGRATED PROCESS

Each of the microorganisms listed herein which are new embodiments and not commercially available have been deposited at the Northern Regional Research Center, located at the U.S. Department of Agriculture, 1815 North University Street, Peoria, Ill. 61604. The accession numbers for each strain so deposited are listed along with the name and description of each microorganism and are identified by the prefix "NRRL". In addition, each such organism has also been deposited at the Institute Armand-Frappier located at 531 Boul. Des Prairies, C.P. 100, Laval, Quebec Canada H7N 4Z3. The accession numbers for each strain so deposited are identified by the prefix "IAF" along with the name and description of each microorganism, together with the NRRL numbers.

1. *Chaetomium cellulolyticum* IAF-101 (NRRL 18756): A new mutant produced by myself which is better than the parent strain (*Chaetomium cellulolyticum* ATCC 32319).

It does not produce toxic metabolites.

The new mutant IAF 101 (NRRL 18756) has a higher growth rate and higher conversion ability to convert lignocellulosic biomass or their fractions (cellulose or hemicelluloses) into protein-rich animal feed or human food than any other microorganisms which could be used in such processes.

3. *Pleurotus sajor-caju* and other Pleurotus spp.; Aspergillus sp. IAF-201 (NRRL 18758) and Penicillium sp. IAF-603 (NRRL 18759) which I have developed. These are also used for the conversion of lignocellulosic biomass into protein-rich feed for animals or food for humans as described above.

4. *Trichoderma reesei* QMY-1(NRRL 18760): A new mutant developed by myself from its parent strain *Trichoderma reesei* QM9414. It is used to produce a complete cellulase-system by growing on lignocellulosic biomass in solid state fermentation (SSF) or in liquid state fermentation (LSF) . This cellulase-system is able to convert 80-90% of lignocelluloses or pure cellulose into simple sugars.

5. Other microorganisms used in this process include *Saccharomyces cerevisiae,* Kluyveromyces sp. and *Zymomonas mobilis* for the fermentation of hydrolysate obtained from enzymatic hydrolysis with the above cellulase-system into ethanol.

As used herein, the term "biomass" includes materials of plant origin. i.e. agricultural residues, wood and forest residues (generally called ligno-celluloses), affluents from wood and pulping and paper industries; manures of animal origin i.e. cattle, swines, poultry, human etc.; and affluents from food factories. All these materials contain cellulose, hemicelluloses, lignin, starch, protein, lipids and some minerals depending on their origin.

DESCRIPTION OF PREFERRED EMBODIMENTS

Lignin in the biomass of plant origin is bonded physically and chemically to the plant polysaccharides, therefore, limited action is performed by microbial hemicellulases and cellulases due to the metabolic blocks of lignin-carbohydrate bonds. Hence, lignin has to be depolymerized, solubilized or removed in order to allow celluloses and hemicellulases to hydrolyse the thus exposed cellulose and hemicelluloses. According to the invention, four different pretreatments can be used, and these will be discussed later.

With reference to the drawings, it will be seen that one ton of biomass 1 essentially made of lignocellulose derived from crop residues, wood or wood residues is pretreated in a manner known per se 2 to be fractionated into approximately 500 kg cellulose 3, 250 kg lignin 4, and 250 kg hemicelluloses 5. About 450 kg of the fractionated cellulose is subjected to enzymatic hydrolysis by treatment 16 with a cellulase enzyme which will be described later to give about 445 kg of a glucose in the hydrolysate at 17. Anaerobic fermentation of the hydrolysate in known manner with yeasts (Sacchoromyces spp. or Kluyveromyces spp.) or bacteria (Zymomonas spp.) at 18 gives about 214.8 kg or 272 liters of ethanol 19. Of course, instead of converting the glucose obtained through enzymatic hydrolysis at 18, into ethanol, glucose could also be converted by fermentation into pharmaceutical products or any other known commercial products.

Separately, a portion of the 250 kg of hemicelluloses 5 is inoculated with Trichoderma reesei QMY-1 (NRRL 18760) to grow an inoculum 9 of Trichoderma reesei QMY-1 (NRRL 18760) which can be combined at 14 with 50 kg of the cellulose obtained at 3 to give a cellulase enzyme which will be used for the cellulose hydrolysis 16 to give glucose, all as mentioned above.

The inoculum of Trichoderma reesei OMY-1 (NRRL 18760) produced at 9 is also used to inoculate protracted bioman at 2 in soljd state or liquid state fermentation for cellulase duction for hydrolysis of cellulose into glucose.

Instead of inoculating the above-mentioned portion of 250 kg of hemicellulose with Trichoderna reesei, one may elect to inoculate the latter with yeasts (e.g. Saccharomyces spp. Kluyveromyces spp.) or bacteria (e.g. Zymomonas spp ) to produce inocula 9 for the direct fermentation of glucose 18 into ethanol 19.

Yet another possibility is to inoculate another portion of 250 kg of hemicellulose with the following microorganisms:

Chaetomium cellulolyticum IAF-101 (NRRL 18756)
Aspergillus sp. IAF-201 (NRRL 18758)
Pleurotus sajor-caju and other Pleurotus spp.
Penicillum sp. IAF-603 (NRRL 18759)

To produce inocula 9 which can be used in step 10 to produce protein-rich animal feed, 11.

The remaining portion of the 250 kg of hemicelluloses is inoculated with any of the five microorganisms 10 for the conversion of the hemicelluloses into protein rich animal feed 11, or food for humans, hereinafter referred to as single-cell protein (SCP).

Any residual mycelial biomass of Trichoderma reesei 15 obtained after the production of the cellulase-system at step 14 is used as animal feed 11. Similarly, any residual microbial biomass of yeasts or bacteria which remains after the ethanol fermentation 18 can be used as animal feed 11.

It will be realized that the bioconversion of hemicelluloses into various inocula can save a lot of glucose produced at 17 otherwise used for such purposes and consequently reducing yields of the final products, for example ethanol 19, or other products.

Pretreated biomass 2 can also be used as such to produce an inoculum of Trichoderma reesei 9 to give the cellulase-system 14 or to ferment with inoculum 9 of any fungus to produce directly at 7 protein-rich animal feed 8.

Finally, a portion of cellulose 3 can also be treated directly by aerobic fermentation at 12 with inoculum 9 of any fungus to produce protein-rich animal feed 13.

Pretreatment 2 may be selected among the following:

1. Alkali Pretreatment

About 70% solubilization of solubilizable matters of a biomass of plant origin is achieved by treating the substrate with 5–20% sodium hydroxide (NaOH) (wt/wt of the substrate) with substrate: water ratio of 1:2 to 1:20 at 80°–121° C. for 30 minutes to 2 hours depending on the nature of the substrate. This treatment solubilizes most of the hemicelluloses and lignin and also makes the cellulose most susceptible for the growth of the microorganisms for the production of protein-rich food/feed or for enzymatic hydrolysis into glucose or for cellulases production.

Pretreated biomass is used as obtained or it can be fractionated into a soluble fraction which contains solubilized hemicelluloses and lignin, and insoluble fraction which contains mostly cellulose and a little lignin and hemicelluloses. The lignin from the soluble fraction is treated by acidification.

2. Chemithermomecanical pulp (CTMP)

Regular size (2–4 cm wide and 0.5–1.0 cm thick) industrial wood chips are used. All chips are screened and washed with water before use. Pulping is carried out in a Sunds Defibrator pilot-plant unit, type 300 CD, using a single-stage pressurized refining.

Wood chips are chemically treated in an impregnator built inside the pilot-plant unit. The thus chemically treated chips are then steamed in the preheater of the unit for five minutes after which they are fed to the refiner for refining.

The conditions used in the pulping process are as follows:

1) Input of chips to the pilot-plant=0.8 kg (on oven-dry weight) per minute.

2) Chemical charge for the treatment of chips, on oven-dry weight of wood: (a) 5 to 10% NaOH and (b) 5% NaOH and 5% $Na_2SO$ 3) Ratio of chemical solution fed to the impregnator to the oven-dry weight of chips fed to the unit: 1:1 (wt/wt).

4) Steam pressure in the preheater: 238 kPa (20 psig) which corresponds to 126° C.

5) Steam pressure for refining 260 kPa (23 psig) which corresponds to 129° C.

6) Clearance between the two flat refining discs: 0.2 mm.

7) Input of water to the flat disc refining zone: 2.3 liters/minute.

8) Clearance between the two cone refining discs: 0.1 mm.

9) Input of water to the cone refining zone: 0.38 liter/minute.

Under the above conditions, the pulp produced has a consistency of approximately 25%. The yield of pulp is about 90% and the resulting pulp has an average size, in terms of Canadian standard freeness, of 100 ml.

The pretreated mass is used as obtained.

3. Steam Pretreatment

In this process steam is added to a digestor where a 1 to 5 minutes residence time at a temperature comprised between 200°–230° C. forces to break the cellulose-hemicellulose and hemicellulose-lignin cleavages. Flash decompression of the treated material forces the needed ultrastructure modifications which frees large fractions of hemicelluloses (75%) and the lignin (80%). The pretreated mass is ready to use as follows:
  i) as obtained,
  ii) washed with water (hemicelluloses-free, i.e. cellulose-lignin complex)
  iii) extracted with ethanol, alkali or other solvents (lignin-free i.e. cellulose).
  iv) water-solubles (hemicelluloses and a little water soluble lignin).

4. Thermomechanical Pretreatment of Aqueous Suspension

A 12–14% solids aqueous suspension is treated at temperatures of 150°–230° C. while being homogenized. Only ground biomass (0.5 mm) can be treated via this method. The residence time can be controlled more precisely than in the so-called stream explosion methods and is typically comprised between 0–2 minutes. As a consequence of this treatment, the hemicelluloses are solubilized together with one third of the lignin. The cellulosic residue has a DP 800–1400.

Removal of the lignin from the residue can be done via simple organo-solvent method, ethanol, water being a convenient system. From this pretreatment the following fractions are available:
  i) the liquid hemicellulose-rich filtrate,
  ii) the residue containing cellulose and lignin,
  iii) the lignin-free residue, cellulose.

By way of examples the compositions of five nutrient media which may be used in the integrated process of the invention will now be given:

| Medium I |
|---|
| (All the requirements are for biomass containing 10 g of glucose equivalent) |
| $(NH_4)_2SO^*_4$ = 1.88–2.357 g |
| $KH_2PO_4$ = 0.75–1.5 g |
| $MgSO_4.7H_2O$ = 0.25–0.5 g |
| $FeSO_4.7H_2O$ = 0.25–5 mg |
| $ZnSO_4.7H_2O$ = 0.25–5 mg |
| Trace element solution* = 0–1 ml |
| water = 1 liter pH = 4–7.5 |
| Boric acid = 114 mg |
| Amonium molybdate = 480 mg |
| cuperic sulphate = 780 mg |
| Manganese chloride = 144 mg |
| Medium II |
| Same as medium I plus |
| $CaCl_2$ = 0.3 g |
| $MnSO_4.7H_2O$ = 1.56 mg |
| Proteose peptone/yeast extract = 0–0.5 g |
| pH = 4–7.5 |
| Medium III |
| (For Yeasts) |
| Same as Medium I plus |
| Yeast Extract = 0.5 g |

| -continued |
|---|
| Water = 1 liter |
| pH 4–7.5 |
| Medium IV |
| (For *Zymomonas mobilis*) |
| Same as Medium I plus |
| Yeast Extract = 1.0 g |
| Water = 1 liter |
| pH 4–7.5 |
| Medium V |
| (For Fermentation of Ethanol) |
| Sugars equivalent to = 80–160 g glucose/L |
| $KH_2PO_4$ = 1.0 g/L |
| $NH_4Cl$ = 1.5 g/L |
| $MgSO_4.7H_2O$ = 0.16 g/L |
| $CaCl_2$ = 0.08 g/L |
| Yeast Extract = 1.0 g/L |

*(or equivalent nitrogen in any other form or in combination thereof or in combination with phosphoric acid which will also eliminate $KH_2PO_4$ from the medium)
*Trace element solution in one liter Each ton of biomass used for the production of ethanol will generate 250–290 kg of hemicellulose sugars. However, some toxic compounds (furfural, hydroxymethyl furfural and phenolic compounds) are produced during pretreatments of lignocelluloses. During the separation of cellulose, all the toxic compounds become part of solubilized hemicelluloses. Therefore, these toxic compounds become a problem for further utilization of hemicelluloses by most microorganisms. The solubilized hemicelluloses contain mostly pentoses (xylose and arabinose), some hexoses (glucose, mannose, galactose), some uronic acids, some solubilized lignin and lignin components.

This hemicellulose fraction is not utilized in almost all the processes for production of protein-rich food/feed. This fraction has also not been economically converted into ethanol because of the presence of toxic compounds. Therefore, hemicellulose fraction ends up as a waste which creates a lot of pollution problem because of its very high BOD.

Keeping in mind that large quantities (250–290 kg/ton of biomass of plant origin) of hemicelluloses are released during pretreatments, the present invention intends to overcome all the prior problems for the utilization of the hemicellulose fraction.

According to the present invention, the hemicellulose fraction is utilized inter alia to produce inocula. The inocula of various microorganisms required in the process according to the present invention are grown in the nutrient media described above. For the production of inocula of *Chaetomium cellulolyticum* IAF-101 (a new mutant), *Pleurotus sajor-caju* and other species of Pleurotus, *Aspergillus* sp. IAF-201 (NRRL 18758) and *Penicillium* sp. IAF-603, (NRRL 18759) the microorganisms are grown on hemicellulose fraction fortified with nutrient medium I, whereas the inoculum of *Trichoderma reesei* QMY-1 (NRRL 18760) is produced on hemicellulose fraction fortified with nutrient medium II. The inocula of yeasts and bacteria (*Zymomonas mobilis*) are produced on hemicelluloses and glucose fortified with medium III and medium IV, respectively.

EXAMPLE I

PRODUCTION OF PROTEIN-RICH FOOD/FEED

1. On Substrate Obtained after Pretreatment

The substrate obtained after pretreatment in a concentration of 1–6% (wt/vol) is fortified with sterile nutrient medium I. As the substrate is sterilized during pretreatment and sterile nutrients are used, there is no need of autoclaving the medium again. The mixture is inoculated with 5-10% (vol/vol) with an inoculum (produced with medium I with a hemicellulose fraction or glucose) of either of the following fungi: *Chaetomium cellulolyticum* IAF-101 (NRRL 18756) species of Pleurotus, Aspergillus Sp. IAF-201 (NRRL 18758) and Penicillium sp. IAF-603 (NRRL 18759). The pH of fermentation is maintained at 4-7.5, preferably at 6. The incubation time varies from 12-72 hours depending upon the concentration of the carbohydrate, the nature of the substrate and its pretreatment. The end-product, protein-rich feed is a mixture of biomass of the above fungi and unutilized cellulose and the unsolubilized lignin and contains 23-50% (dry wt basis) crude protein depending on the substrate and the fungus used.

2. On Hemicellulose Fraction

A hemicellulose fraction containing 1-6% (wt/vol) carbohydrates is fortified with nutrient medium I, autoclaved at 121° C. for 20-30 minutes, and cooled at 25°-40° C. It is inoculated with 5-10% (vol/vol) inoculum (produced as described above) of either of the following fungi: *Chaetomium cellulolyticum* IAF-101 (NRRL 18756), *Pleurotus sajor-caju* or other species of Pleurotus, Aspergillus sp. IAF-201 (NRRL 18758) and Penicillium sp. IAF-603 (NRRL 18759). The pH of fermentation is maintained at 4-7.5, preferably at 6. The incubation time varies from 12-72 hours depending upon the concentration of the carbohydrates and the nature of the substrate used to obtain hemicellulose fraction. The end-product, protein-rich food/feed is a biomass of the above fungi containing 37-50% (dry wt basis) crude protein.

3. On Cellulose Fraction

A cellulose fraction whose concentration is from 1 to 6% (wt/vol) is fortified with nutrient medium I, autoclaved at 121° C. for 30 minutes to one hour depending on the concentration of cellulose in the medium, and cooled to 25°-40° C. It is inoculated with an inoculum produced on a hemicellulose fraction as described above) of either of the following fungi: *Chaetomium cellulolyticum* IAF-101 (NRRL 18756), species of Pleurotus, Aspergillus sp. IAF-201 (NRRL 18758) and Penicillium sp. IAF-603 (NRRL 18759). The pH of fermentation is maintained at 4-7.5, preferably between 5.5 and 6.0. The incubation time varies from 20 to 72 hours depending on the concentration of the cellulose in the medium. The end-product, protein-rich food/feed is a biomass of the above fungi containing 37-50% (dry wt basis) crude protein.

The nutrients given in the medium I are for a substrate equivalent to 10 g glucose. The quantities of nutrients are increased with the increase of the concentration of the substrate in the medium.

The concentrations of the substrates (as described in 1, 2 and 3 above) are increased by a fed-batch method i.e. starting the fermentation initially with 2-3% and then adding the rest of the substrate at various intervals according to the growth rate of the particular fungus. The interval varies from 5-12 hours.

The temperature of fermentation is 30°-40° C. preferably at 37° C. for *Chaetomium cellulolyticum* IAF-101(NRRL 18756), Aspergillus sp. IAF-201 (NRRL 18758), but for species of Pleurotus and Penicillium.sp. IAF-603 (NRRL 18759) it is 25°-37° C. preferably 30° C.

4. On Manures

The manures are fractionated into two phases: (i) a liquid phase containing soluble carbohydrates, starch, protein, lipids, etc. and (ii) a solid phase contains cellulose, hemicelluloses and lignin. The solid phase is composed of cellulose, hemicelluloses and lignin and is converted into protein-rich feed as described above under 1, 2, and 3.

The liquid phase is fortified with 0 to 0.12% (wt/vol) $(NH_4)_2SO_4$ as desired and is autoclaved at 121° C. 30 minutes. It is converted into protein-rich feed by inoculation with the following fungi (grown on hemicellulose fraction): *Chaetomium cellulolyticum* IAF-101 (NRRL 18756), spacies of Pleurotus, Aspergillus. sp IAF-201 (NRRL 18758), and Penicillium sp IAF-603 (NRRL 18759). The end-product is a biomass of these fungi containing 30-37% crude protein.

The liquid phase is mixed with a hemicellulose fraction or a cellulose fraction in various ratio 1:1 to 1:10 and is fortified with 0 to 0.12% (wt/vol) $(NH_4)SO_4$ as desired. The mixture is autoclaved at 121° C. for 30 minutes. It is inoculated with the following fungi (grown on hemicellulose fraction): *Chaetomium Cellulolyticum* IAF-101 (NRRL 18756), species of Pleurotus, Aspergillus sp. IAF-201 (NRRL 18758), and Penicillium sp. IAF-603 (NRRL 18759). The end-product is a biomass of these fungi containing 37-50% crude protein.

The end-product is harvested by passing through 3 layers of cheese cloth, pressed and dried to about 10% moisture. During harvesting all the solubilized lignin and toxic compounds become the part of the filtrate which can be precipitated by acidifying the filtrate to pH 3.5. The latter can be used for making adhesive and other chemicals or could be used as fuel for burning. Therefore, at the end of this process there are no affluents which could cause any pollution problems.

EXAMPLE II

Production of Ethanol

1. Production of Cellulase-System

The cellulase-system is produced on pretreated biomase which has not been fractionated or on fractionated cellulose. The pretreated biomass or fractionated cellulose is fermented aerobically with *Trichoderma reesei* QMY-1 (NRRL 18760).

Fifty Kg of cellulose or 100 Kg of pretreated biomass (FIG. 1) is required for producing sufficient enzyme-system to hydrolyze 450 Kg of cellulose (FIG. 1).

The cellulase-system can be produced by solid state fermentation (SSF) or liquid state fermentation (LSF). According to the invention, the hemicelluloses and lignin are preferably kept along with the cellulose, thus there is no fractionation of pretreated biomass. In SSF the nutrient medium II is mixed well and the moisture is maintained from 60-85% (wt/wt) so that there is no free water. The pH is adjusted between 5-7. It is autoclaved at 121° C. for 30 minutes to 1 hour depending on the depth of the substrate. The preferable depth is 2-3 cm. The substrate is spread in a steel tray of any convenient size with a 40 mesh screen at the bottom for aeration. The tray is covered with a steel lid to avoid contamination. The cultures are inoculated with *Trichoderma reesei* QMY-1 (NRRL 18760) grown on hemicellulose fraction. The inoculum is used in an amount of 50–100 ml (containing about 0.5–1.0 g (dry wt) mycelium for 100 g (dry wt) of substrate.

The trays are kept in a humidified (about 80% relative humidity) incubator maintained at 25°–37° C., preferably 30° C.

After 2–6 weeks growth depending on the nature of the substrate used, the fermented substrate is shaken with water in a ratio of 1:20 for about ½ hour. It is centrifuged, after which the supernatant serves as a cellulase-system for the hydrolysis of cellulose to give a glucose solution. The cellulase system is also utilized to hydrolyze pretreated biomass without fractionation to give a mixture of glucose, xylose, galactose, mannose, arabinose, etc.

The cellulase-system can also be prepared in LSF on pure cellulose or pretreated unfractionated biomass at a concentration of 2–16 with nutrient medium II. The concentration of the substrate is increased steadily by the fed-batch method. The enzyme broth is separated as explained above.

2. Hydrolysis of Cellulose

The enzyme-system produced in SSF on pretreated but unfractionated biomass contains: cellulase 5–20 IU/ml, B-glucosidase 5–20 IU/ml, and xylanases 300–800 IU/ml. Higher concentrations of enzymes can be obtained by extracting the cellulase-system with a small quantity of water. This enzyme system can hydrolyze 80–90% of cellulose. The hydrolyzate contains 9–15% glucose syrup with very little cellobiose. In this cellulase-system there is no need of addition of extra β-glycosidase or xylanases as is done in a number of known processes of the prior art. Similarly the enzyme-system produced in LSF has almost the same ratios of various enzymes except that the enzyme activity may be a little less.

3. Ethanol Fermentation

The inocula of yeasts and bacteria, required for the fermentation of the hydrolysate are grown on hemicellulose fraction or glucose fortified with the nutrient medium III and nutrient medium IV, respectively.

The hydrolysate obtained from the enzymatic hydrolysis of cellulose containing 10–15% (wt/vol) glucose is fortified with nutrient medium V. Fermentation is carried out at 25°–30° C. for 24–72 hours depending on the concentration of glucose in the medium, the type of organism used and the amount of inoculum of yeast or bacteria used.

The fermentation of glucose into ethanol could be carried out even without the addition of any nutrients (Medium V) as some residual nutrients are brought in during hydrolysis from the medium in which the cellulase-system was produced and also some from the medium in which the inocula of yeasts or bacteria were produced.

4. Hydrolysis of Hemicelluloses

The hemicellulose fractions obtained by various pretreatments (1,2,3 and 4) still contain polymers, oligomers or even dimers of various sugars (xylose, mannose, galactose, arabinose and glucose). Most of the microorganisms cannot metabolize for microbial protein production or cannot catabolize for ethanol or other solvent production. However, the enzyme-system produced here in SSF or LSF contains very high amount of hemicellulases (measured as xylanase in this case) and can be used to hydrolyze the hemicellulose fraction into its monomer sugars. The microorganisms being used in this case do not need any such hydrolysis of hemicelluloses for the production of protein-rich feed because these microorganisms already have the ability to hydrolyze the hemicelluloses into simple sugars (monomers).

The production of food, feed and fuel by the integrated process according to the invention leaves nothing unutilized, which means that there is no effluent disposal problem. In addition, because of the complete utilization of hemicelluloses, the process is more economical than those presently known.

It is recommended that a forest biomass especially one derived from poplar trees be used as a major feedstock, although other wood species and other lignocellulosic materials are used.

Preliminary feeding trials on rats indicated that up to 20–40% of the total protein requirement can be replaced by the protein produced according to the present invention without any pathological symptoms.

I claim:

1. Process for treating biomass which comprises:
   (a) pretreating said biomass to enable it to be fractionated into cellulose, lignin and hemicellulose;
   (b) separating pretreated biomass into said celulose lignin and hemicellulose;
   (c) producing inocula of Chaetomium cellulolyticum IAF-101 (NRRL 18756), Aspergillus sp. IAF-201 (NRRL 18758), Penicillum sp. IAF-603 (NRRL 18759), Trichoderma reesei QMY-1 (NRRL 18760), Saccharomyces spp., Kluyveromyces spp., and Zymononas spp. by growing same on hemicellulose fraction obtained by separation from pretreated biomass;
   (d) inoculating another hemicellulose fraction obtained by separation from pretreated biomass with an inoculum selected from the group consisting of inocula of Chaetomium cellulolyticum IAF-101 (NRRL 18756), Aspergillus sp. IAF-201 (NRRL 18758) and Penicillm sp. IAF-603 (NRRL 18759) under aerobic fermentation conditions effective to produce protein-rich animal feed;
   (e) providing a fraction of pretreated biomass not subjected to separating step (b) and inoculating same with an inoculum of Chaetomium cellulolyticum IAF-101 (NRRL 18756), Aspergillus sp. IAF-201 (NRRL 18758) or Penicillum sp. IAF-603 (NRRL 18759) under aerobic fermentation conditions effective to product protein-rich animal feed;
   (f) inoculating a cellulose fraction obtained by separation from pretreated biomass with an inoculum selected from the group consisting of inocula of Chaetomium cellulolyticum IAF-101 (NRRL 18756), Aspergillus sp. IAF-201 (NRRL 18758) and Penicillum sp. IAF-603 (NRRL 18759) under aerobic fermentation conditions effective to produce protein-rich animal feed;
   (g) fermenting a fraction of pretreated biomass not subjected to separating step (b) or fractionated cellulose under aerobic conditions with Trichoderma reesei QMY-1 (NRRL 18760) to give a cellulase-system, hydrolyzing a cellulose fraction obtained in step (d) with said cellulose system to give glucose, and fermenting said glucose with an inoculum selected from said inocula of yeasts and bacteria to give ethanol.

2. Process according to claim 1, wherein protein-rich animal feed obtained from step (f) can be mixed with protein-rich animal feed obtained in step (d).

3. Process according to claim 1, wherein said biomass is lignoceluloses, forest biomass and agricultural residues.

4. Process according to claim 1, wherein said biomass is manure.

5. Process according to claim 1, wherein said biomass is pretreated with an alkali.

6. Process according to claim 5, wherein said biomass is mixed with water in a weight ratio of 1:2 to 1:20, mixture is pretreated with 5-20 weight percent sodium hydroxide with respect to the weight of the biomass at about 80°-121° C. for 30 minutes to 2 hours.

7. Process according to claim 1(c), wherein said hemicellulose fraction is fortified with a nutrient medium before inoculating same.

8. Process which comprises pretreating a biomass to enable it to be fractionated into cellulose, lignin and hemicellulose, separating pretreated biomass into said celulose, lignin and hemicellulose, providing inocula of *Chaetomium cellulolyticum* IAF-101 (NRRL 18756), Aspergillus sp. IAF-201 (NRRL 18758), Penicillum sp IAF-603 (NRRL 18759), by growing same on hemicellulose fraction obtained by separation from pretreated biomass; and inoculating another hemicellulose fraction obtained by separation from pretreated biomass with an inoculum selected from said inocula under aerobic fermentation conditions effective to produce protein-rich animal feed.

9. Process which comprises pretreating a biomass to enable it to be fractionated into cellulose, lignin and hemicellulose, separating pretreated biomass into said cellulose, lignin and hemicellulose, providing inocula of *Chaetomium cellulolyticum* IAF-101 (NRRL 18756), Aspergillus sp. IAF-201 (NRRL 18758), Penicilum sp. IAF-603 (NRRL 18759), by growing same on hemicellulose fraction obtained by separation from pretreated biomass, providing a fraction of pretreated biomass not subjected to said separating step and inoculating same with an inoculum selected from said inocula under aerobic fermentation conditions effective to produce protein-rich animal feed.

10. Process which comprises pretreating a biomass to enable it to be fractionated into cellulose, lignin and hemicellulose, separating said pretreated biomass into said cellulose, lignin and hemicellulose, providing inocula of *Chaetomium cellulolyticum* IAF-101 (NRRL 18756), Aspergillus sp. IAF-201 (NRRL 18758), Penicillum sp. IAF-603 (NRRL 18759), by growing same on hemicellulose fraction obtained by separation from pretreated biomass, providing a fraction of pretreated biomass, inoculating a cellulose fraction obtained by separation from pretreated biomass with an inoculum selected from the group consisting of said inocula under aerobic fermentation conditions effective to produce protein-rich animal feed.

11. Process which comprises pretreating a biomass to enable it to be fractionated into cellulose, lignin and hemicellulose, separating said pretreated biomass into said cellulose, lignin and hemicellulose, providing inocula of *Trichoderma reesei* QMY-1 (NRRL 18760), yeast and bacteria by growing same on hemicellulose fraction obtained by separation from pretreated biomass or on glucose, fermenting a fraction of pretreated biomass not subjected to said separating step or fractionated cellulose under aerobic conditions with an inoculum of *Trichoderma reesei* QMY-1 (NRRL 18760) to give a cellulase-system, hydrolyzing a cellulose fraction obtained in said separating step with said cellulase-system to give glucose, and fermenting said glucose with an inoculum selected from said inocula of yeasts and bacteria to give ethanol.

12. Process which comprises subjecting pretreated biomass to solid state or liquid fermentation with *Trichoderma reesei* QMY-1 (NRRL 18760) to give a cellulase system.

13. Process according to claim 12 which comprises preheating biomass to enable it to be fractionated into cellulose, lignin and hemicellulose, separating hemicelluloses from said pretreated biomass, hydrolyzing said hemicelluloses with said cellulase system to give monomer sugars.

14. Process according to claim 13, wherein said sugars are selected from the group consisting of xylose, galactose, arabinose, mannose and glucose.

* * * * *